United States Patent [19]

Kim

[11] 4,109,530
[45] Aug. 29, 1978

[54] SPECIMEN TRANSFER CONTAINER

[75] Inventor: Hyun Jung Kim, Cherry Hill, N.J.

[73] Assignee: Steven M. Diamond, Easton, Pa.; a part interest

[21] Appl. No.: 792,214

[22] Filed: Apr. 29, 1977

[51] Int. Cl.² .............................................. G01F 11/28
[52] U.S. Cl. .................... 73/427; 73/421 R; 128/2 F; 128/295
[58] Field of Search .................. 73/421 R, 171, 427; 128/2 F, 295

[56] References Cited

U.S. PATENT DOCUMENTS

| 756,109 | 3/1904 | Friez | 73/171 |
|---|---|---|---|
| 2,161,060 | 6/1939 | Kelsey | 73/427 X |
| 2,711,099 | 6/1955 | Hastings | 73/171 |
| 3,543,743 | 12/1970 | Foderick | 128/2 F |
| 3,635,091 | 1/1972 | Linzer et al. | 73/421 R |
| 3,711,871 | 1/1973 | Sherin | 128/2 F |
| 3,727,603 | 4/1973 | Holbrook | 128/2 F |
| 3,831,453 | 8/1974 | McWhorter | 128/2 F X |
| 3,878,571 | 4/1975 | Seeley | 128/2 F |
| 3,888,236 | 6/1975 | Marx | 128/2 F |

*Primary Examiner*—Daniel M. Yasich
*Attorney, Agent, or Firm*—James Albert Drobile

[57] ABSTRACT

A liquid specimen transfer container, designed to prevent contamination, provides two interconnected storage chambers. The first chamber receives donor inputs via an integral basin which prevents splashing. Input in excess of a measured volume overflows into the second storage chamber for retention and later recovery. A removable closure such as a cap or plug, or suitable valve means such as a rupturable seal, prevents discharge of liquid from first chamber until the transfer container is connected to a receiving vessel such as a laboratory test instrument requiring a measured sample.

4 Claims, 3 Drawing Figures

SPECIMEN TRANSFER CONTAINER

BACKGROUND OF THE INVENTION

The present invention relates generally to a container for receiving, storing and transferring a specimen of a body fluid such as urine, and more particularly to a transfer container to accommodate the handling of fluids which may contain a contagious disease substance such as, for example, urine containing infectious hepatitis bodies. Infectious hepatitis can be contracted merely by touching such a fluid, and laboratory personnel are understandably concerned about their exposure to the disease due to handling specimens of the fluid under conditions where direct contact of the fluids with the skin is possible. These hazardous conditions arise most commonly during the procedures employed in sampling and testing when the urine sample is first acquired in a sample container, when a measured sample is removed from the main body of liquid, and when the measured sample is introduced into the testing instrument.

A corollary problem of contamination arises from the complexity of the devices now in use for specimen collection and sampling. Extended lengths of tubing and valving to duct the specimen into a collection container, and extended tubes and valving to withdraw a measured sample for testing leave many wet and contaminated surfaces and collection points for stray droplets which can subsequently contaminate an unwary person including hospital aides and medical technicians. Additionally, the complexity of known devices increases their cost of production. United States Pat. Nos. 3,831,453; 3,727,603; and 3,699,815 illustrate devices which are representative of the present state of art in this field.

What has long been needed is a transfer container for receiving, storing, and measuring and dispensing a specimen of contaminated liquid which is simple and inexpensive in construction and use. Such a device should directly receive the liquid sample from the subject patient without usage of intermediate ducts and valves, and similarly should permit direct discharge from the device of a precisely measured quantity of specimen, drawn from the entire collection, without use of complex valves and ducts. A measured specimen from the transfer container should discharge directly into the laboratory test apparatus without need for ducts or complex valving. Additionally, the transfer container should be protectively sealed against leakage at both inlet and outlet to enable safe storage, transport and handling of the transfer container between the time of specimen acquisition and laboratory test.

The present invention is a container comprising a pair of vertically oriented and conveniently but not necessarily cylindrical and concentric chambers. The inner chamber has at its top a concave, conveniently funnel-like rim of expanded diameter for receiving an input of specimen liquid without splashin or overflow. The discharge end of the inner chamber is sealed by a removable closure or plug, or by a suitable normally closed valve means such as a stop cock or a readily rupturable membrane. The internal volumes of both chambers are entirely isolated and sealed, one from the other, except for overflow passage means, conveniently consisting of a ring of overflow holes circling the inner cylinder, communicating between the two storage chambers, and additionally passage means, conveniently consisting of a small plurality of holes in the concave funnel surface, which connect the outer storage chamber to the inlet region. The volume of liquid stored in the inner chamber between the closure, plug or valve means and the overflow passage means (e.g., the ring of overflow holes) equals the precise amount of specimen required for subsequent laboratory testing. Surplus or additional liquid received in the inner chamber is collected in the outer chamber via the overflow passage means, e.g., holes. Plastic caps may be provided to snap over the inlet and outlet ends of the container during storage and transport, and the latter cap may serve as the closure referred to hereinabove.

Graduation markings conveniently may be provided on the walls of either or both chambers, to indicate the volume of liquid stored in the chamber or chambers, and liquid can be transferred from the outer storage chamber through the passage means, e.g., hols, in the funnel-like wall and into the inner chamber.

In use the tube of the test instrument which contains reagent chemicals is connected in sealing engagement with the outlet of the container, the removable closure or plug is removed, or the valve means is opened (e.g., the rupturable membrane is ruptured), and the measured quantity of sample is allowed to flow from the inner chamber, and to flow into the test instrument and react with the chemicals therein .

Accordingly, an object of the present invention is to provide a transfer container which dispenses one or more measured samples from a collected liquid sample.

Another object of the present invention is to provide a transfer container which receives liquid specimens directly at its input without splashing or overflow of liquid, and without complex valving.

It is a further object of the present invention to provide a transfer container, which provides a direct outlet for specimen samples without use of complex valving.

Yet another object of the present invention is to provide a transfer container which is simply sealed at inlet and outlet for storage and transport.

Still another object of the present invention is to provide a transfer container which retains overflow liquid and makes overflow liquid available for additional measured samples.

A still further object of the present invention is to provide a transfer container which is simple in construction, simple and safe to use, and economical to produce.

Other objects, advantages and novel features of the present invention will become apparent from the following detailed description of the invention when considered in conjunction with the accompanying drawings in which.

Figure 1:
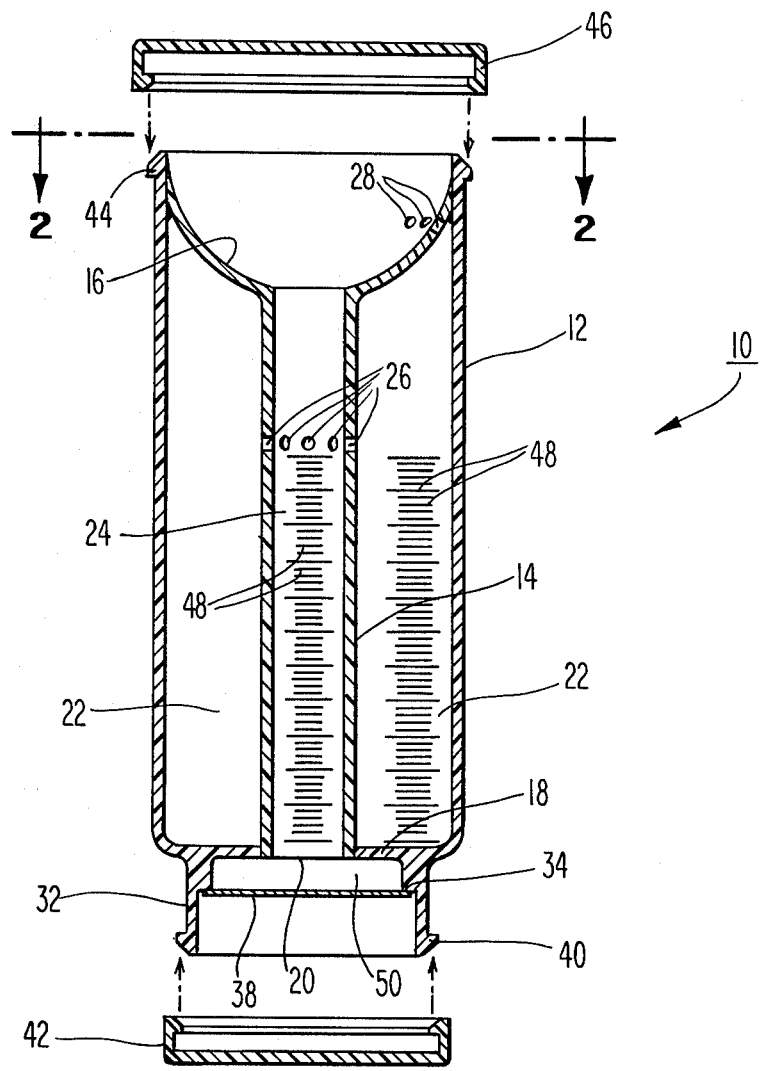
FIG. 1 is a sectional elevation view of one preferred embodiment of the transfer container of this invention taken along line 1—1 of FIG. 2, and with end caps shown as detached.
Figure 2:
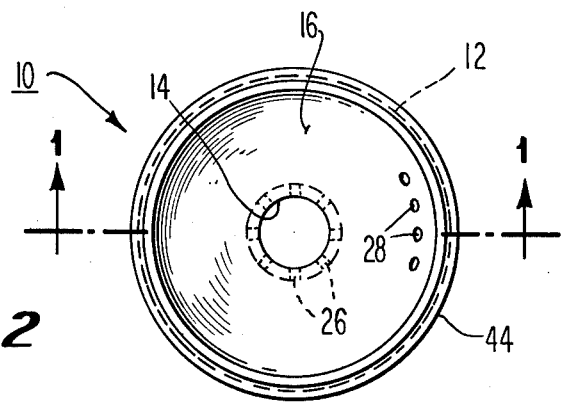
FIG. 2 is a top view of the transfer container taken along the line 2—2 of FIG. 1.

Referring to FIGS. 1 and 2, the transfer container 10 of this invention for receiving, storing and dispensing of liquid specimens is comprised of the outer cylinder 12 and the inner cylinder 14 located concentrically therein. A funnel-shaped receiving basin 16, concave side upward, surmounts the inner cylinder 14, and bridges between the inner cylinder 14 and the outer cylinder 12. The lower end 18 of the outer cylinder 12 turns inward to abut the lower end 20 of the inner cylinder 14, thereby providing the outer annular storage chamber 22 generally isolated from the inner cylindrical storage chamber 24.

A horizontal circle of small holes 26 (as seen in FIG. 1) through the wall of the inner cylinder 14 provide communication between the inner storage chamber 24 and the outer storage chamber 22 and serve as the passage means for overflow of liquid in excess of the measured sample. A plurality of small apertures 28 through the receiving basin 16 serve as additional passage means and permit liquid in the outer storage chamber 22 to enter the basin 16 as explained more fully hereinafter.

The outlet from the transfer container 10, as shown in FIG. 1, is a circular neck 32 having an internal shoulder 34. The internal diameter of the neck 32 below the shoulder 34 is suited to receive the inlet tube or end of the laboratory test instrument (not shown) which is to utilize a measured sample from the container 10. Valve means, shown in FIG. 1 as a rupturable seal 38 extending across internal shoulder 34 and covering the adjoining opening, prevents escape of liquid during periods of transport and storage of the container 10. The outlet neck 32 of container 10 flares out at the discharge end 40 to allow attachment of a conventional flexible plastic cap or cover 42 which is pressed into place to prevent damage to the rupturable seal 38. The upper edge 44 of the outer cylinder 12 is similarly flared and provided with a conventional flexible and preferably elastic plastic cap or cover 46 which is pressed into place to seal in a collected specimen.

It should be noted that the location of the rupturable seal 38, when employed, is not critical, except that it preferably should be so located as to be rupturable without leakage of the specimen from the container. Thus, in the container illustrated in FIGS. 1 and 2, it may be located on or near the shoulder 34, or over the outlet edge 40, or in between those locations. It also may be located over the outlet 20 of inner chamber 24 of container 10.

The transfer container 10 conveniently may be, but need not be, fabricated from a substantially transparent material, such as glass or a polyolefin, so that the quantity of liquid in each storage volume, 22 and/or 24, can be readily observed. As noted hereinabove, graduation markings 48 may be provided on both cylinder walls so that the total volume of specimen in the container 10 can be readily determined as the sum of both graduation readings.

All joining surfaces are sealed in fabrication, e.g., by using adhesives or heat fusion, such that the outer chamber 22 is isolated from the inner chamber 24 and the receiving basin 16 except by communication through the aforementioned passage means provided by holes 26 and apertures 28. The volume of liquid storable between the rupturable seal 38 at the bottom of the container 10 and the circular row of holes 26 in the wall of the inner cylinder 14, i.e., the total of volumes indicated as 24 and 50 in FIG. 1, is precisely equal to the sample size required for input to the laboratory test instrument.

Usage of the transfer container 10 is described hereinafter for the collection of urine although it will be readily apparent that other liquids can be similarly processed. Urine is discharged by the donor directly into the receiving basin 16. The concave shape of the basin 16 receives the liquid without splashing. The liquid, by gravity feed, flows into the central cylinder 14, first filling the volume 50 above the rupturable seal 38, and then filling the volume of the inner storage chamber 24 up to the row of holes 26. Additional liquid entering the inner cylinder 14 overflows into the outer storage chamber 22 via the overflow holes 26, whereby no more than the desired, measured quantity is retained in the inner chamber 24 and volume 50.

If the container 10 is to be stored or transported, the top and bottom sealing covers 46 and 42 are pressed into place. When the measured sample is to be dispensed, the lower cover 42 is removed, and the container 10 is pressed in sealing engagement onto the inlet tube (not shown) of the test instrument. The inlet tube is inserted until it rests against the shoulder 34 in the neck 32. The inlet tube may be so configured, and the rupturable seal 38 so positioned, that the seal 38 is ruptured by the final positioning of the inlet tube. Alternatively, and preferably, the seal can be ruptured by the application of pressure created by substantially depressing (as by the application of a finger) the flexible, elastic top cap 46. With the membrane 38 ruptured, and upon removal of the top cover 46, the liquid discharges directly from the measured chambers 24 and 50 into the test instrument. Additional liquid for additional samples can be retrieved from the outer storage chamber 22 by tilting the container 10 into an upside-down position and allowing liquid to enter the basin 16 via the passage apertures 28. Upon repositioning the container 10 upright, the liquid from the basin 16 enters the inner cylinder 14 as described above.

It should be understood that, if during transport or storage the transfer container 10 is inadvertently not maintained vertically upright, liquid may leave the inner chamber 24 and enter the outer storage chamber 22 via the holes 26 and apertures 28. This condition can be rectified preparatory to dispensing a sample by means of the tilting procedure described above.

Figure 3:
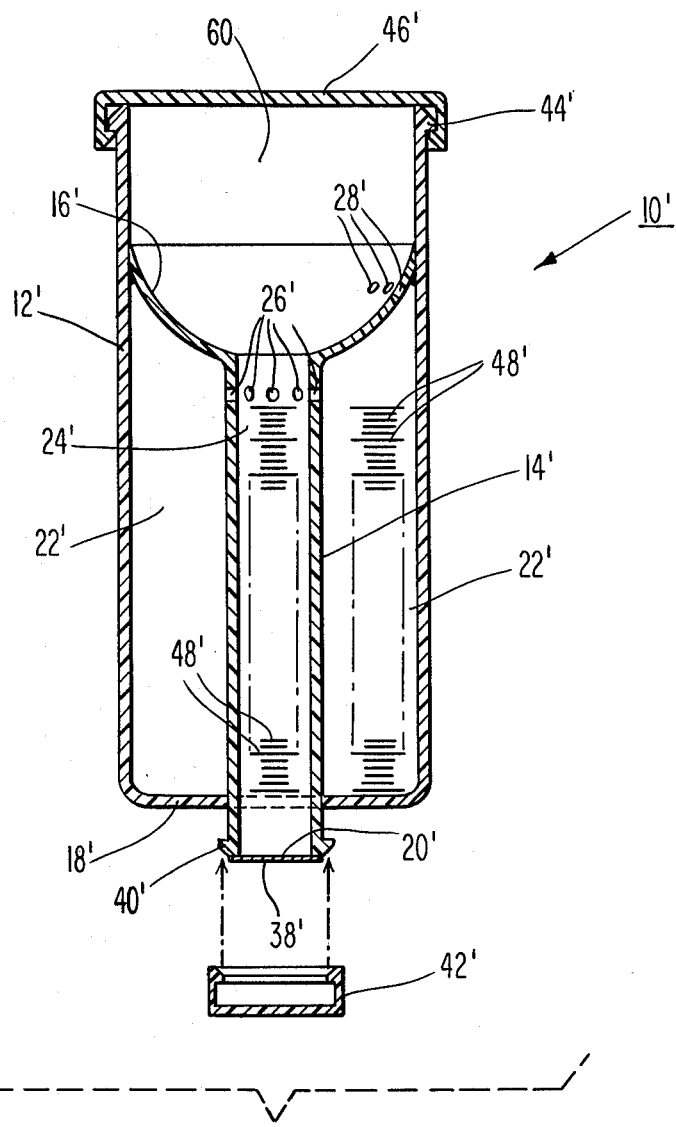
FIG. 3 is a view of an alternative preferred embodiment of the invention.

In an alternative, preferred embodiment of this invention, shown in FIG. 3, the upper portion 60 of the inner cylinder 14' is enlarged in diameter somewhat above the overflow holes 26'. This enlargement 60 in the inner cylinder 14' is such that the storage volume in the inner cylinder 14' between the upper edge 44' and the level of the row of holes 26' equals or exceeds the volume between the discharge end 40' and the row of holes 26'. Corresponding parts in FIG. 3 have been indicated by use of the prime (') marking.

Thus, by inverting the sealed container 10', enough liquid, if available, is retrieved from the outer storage chamber 22' to provide a full sample of measured quantity, as before, in the inner chamber 24' when the container 10' is returned to its upright position.

In order to illustrate a specific embodiment of the invention, a transfer container is fabricated from substantially transparent, rigid polyethylene of approximately one-sixteenth inch thickness in conformity with the structure illustrated in FIG. 3. The inside diameter of outer cylinder 12' is 4.5 centimeters, while the inside diameter of inner cylinder 14' is 1.8 centimeters. The over-all length of outer cylinder 12', from its upper edge 44' to its juncture with the bottom 18' of inner cylinder 14', is 14.8 centimeters. Inner cylinder 14' extends beyond the bottom 18' of outer cylinder 12' by a distance of approximately 2 centimeters. The outlet 20' of inner cylinder 14' is covered by a readily-rupturable thin plastic seal 38', which is fastened by a suitable adhesive to the annular face of cylinder end 40'. A plurality of overflow holes 26' are provided in the wall of inner cylinder 14' along a perimeter which is 1 centimeter below the bottom of funnel-shaped receiving basin 16', and 5 centimeters below the top edge 44' of outer cylinder 12'. Top edge 44' is provided with removable, flexible and elastic, plastic cap or cover 46', and the discharge end 40' (also 20') of inner cylinder 14' also is provided with a removable, flexible cap or cover 42'. Holes 28', which serve as a communicating liquid passage between reservoir 60 and outer chamber 22', are provided in funnel-shaped receiving basin 16' as shown in FIG. 3. The volume of inner chamber 24' (i.e., between holes 26' and the top of seal 38' at opening 20' of inner cylinder 14') is 25 cubic centimeters. The volume of the outer chamber 22', from the bottom of said chamber 22' up to holes 26', is approximately 130 cubic centimeters. The capacity of reservoir 60 (i.e., volume between top edge 44' and holes 26') is approximately 60 cubic centimeters. The inner cylinder 14' and the outer cylinder 12' are conveniently marked, as shown, with graduations 48' to facilitate the determination of the contents in each chamber.

The specimen transfer container fabricated as illustrated in FIG. 3 and in accordance with the above-stated specifications, is used to collect and store a urine specimen, and to measure a precise 25 cubic centimeter sample of such specimen and dispense that sample directly into a testing apparatus. These procedures were carried out with the attendant benefits hereinabove described for the invention, i.e., without spillage or leakage of the liquid container contents and consequent undesirable, direct contact between such contents and the skin of the handler or handlers.

In another alternative embodiment of the transfer container of this invention, the outlet end of the container 10 may narrow down and include a valve, e.g., a stop-cock, which is used to release the measured quantity of liquid rather than the rupturable seal 38 and cover 42 as described above. In still another embodiment, the valve means (e.g., the rupturable seal or the stop-cock) may be entirely omitted and closure achieved through the use of the lower cap or cover alone.

From the preceding description it is evident that the objects of the invention are attained and although the invention has been described in detail, it should be understood that the description is by way of illustration and example only. The spirit and scope of this invention are limited only by terms of the appended claims.

The invention claimed is:

1. A transfer container for the receiving, storing and dispensing of liquid specimens including:
    a cylindrical first storage chamber having an open top inlet and an open bottom outlet;
    a sealed annular second chamber encircling said first storage chamber, being concentric therewith, and having a common wall therebetween;
    an outwardly open receiving basin forming the upper wall of said second storage chamber and having a discharge outlet connected to said open top inlet of said first storage chamber;
    first passage means interconnecting said first storage chamber and said second storage chamber, said first passage means consisting of a plurality of apertures in said common wall between said first storage chamber and said second chamber at a location above said bottom outlet in said first storage chamber, whereby liquid in said first storage chamber can overflow into said second storage chamber;
    second passage means interconnecting said second storage chamber and said receiving basin, said second passage means consisting of a plurality of apertures in the common wall between said basin and said second storage chamber, whereby liquid in said second storage chamber can flow into said basin; and
    normally closed closure means adapted to open selectively open said bottom outlet of said first storage chamber.

2. The transfer container of claim 1 wherein said closure means includes a thin, flexible and readily-rupturable seal, said seal being readily-ruptured by pressure.

3. The transfer container of claim 2 further including a removable flexible elastic cover adapted to seal said open receiving basin and, by being substantially inwardly depressed, creating a pressure against said readily-rupturable seal sufficient to rupture same.

4. The transfer container of claim 2 wherein the bottom outlet in said first storage chamber is sized to be adapted for the insertion of a discharge tube in sealing engagement, whereby said readily-rupturable seal is ruptured and said first storage chamber is discharged without leakage.

* * * * *